(12) United States Patent
Liu

(10) Patent No.: US 11,489,227 B2
(45) Date of Patent: Nov. 1, 2022

(54) ELECTRONIC CIGARETTE

(71) Applicant: Tuanfang Liu, Shenzhen (CN)

(72) Inventor: Tuanfang Liu, Shenzhen (CN)

(*) Notice: Subject to any disclaimer, the term of this patent is extended or adjusted under 35 U.S.C. 154(b) by 933 days.

(21) Appl. No.: 16/275,286

(22) Filed: Feb. 13, 2019

(65) Prior Publication Data

US 2020/0138110 A1    May 7, 2020

(30) Foreign Application Priority Data

Nov. 6, 2018 (CN) .......................... 201811310583.2
Nov. 6, 2018 (CN) .......................... 201821815064.7

(51) Int. Cl.
*H01M 50/209*    (2021.01)
*A24D 3/10*    (2006.01)
*A24F 7/04*    (2006.01)
*H01M 10/42*    (2006.01)
*H05B 3/46*    (2006.01)

(52) U.S. Cl.
CPC ............ *H01M 50/209* (2021.01); *A24D 3/10* (2013.01); *A24F 7/04* (2013.01); *H01M 10/425* (2013.01); *H05B 3/46* (2013.01); *H01M 2010/4271* (2013.01); *H01M 2220/30* (2013.01)

(58) Field of Classification Search
CPC ............ H01M 50/209; H01M 10/425; H01M 2010/4271; H01M 2220/30; H05B 3/46; A24D 3/10; A24F 7/04

USPC ......................................................... 131/329
See application file for complete search history.

(56) References Cited

U.S. PATENT DOCUMENTS

| 9,986,762 | B2 * | 6/2018 | Alarcon | .................. A24F 40/46 |
| 10,015,992 | B2 * | 7/2018 | Li | .......................... A24F 40/485 |
| 2017/0281883 | A1 * | 10/2017 | Li | ........................ A61M 11/041 |

FOREIGN PATENT DOCUMENTS

| CN | 207744705 U | * | 8/2018 | |
| CN | 207855045 U | * | 9/2018 | ............. A24F 40/40 |

* cited by examiner

*Primary Examiner* — Peter G Leigh
(74) *Attorney, Agent, or Firm* — Matthias Scholl P.C.; Matthias Scholl

(57) ABSTRACT

An electronic cigarette, including an atomizing assembly and a battery assembly. The atomizing assembly is disposed on the battery assembly. The atomizing assembly includes a mouthpiece, a filter cotton, a guide tube, an e-liquid container, a first sealer adapted to seal the e-liquid container, a heating wire comprising a pin, a barrier, a base, a second sealer adapted to seal the base, an insulation ring, and electrodes. The battery assembly includes a battery frame, a light guide, a silica gel, a fixed seat, a printed circuit board assembly, and a battery cell. The guide tube is disposed in the e-liquid container. The heating wire is disposed on the barrier. The barrier is disposed in the base. The insulation ring passes through the pin of the heating wire and is fixed in the base. The electrodes are disposed in the insulation ring.

2 Claims, 5 Drawing Sheets

ELECTRONIC CIGARETTE

CROSS-REFERENCE TO RELAYED APPLICATIONS

Pursuant to 35 U.S.C. § 119 and the Paris Convention Treaty, this application claims foreign priority to Chinese Patent Application No. 201811310583.2 filed Nov. 6, 2018, and to Chinese Patent Application No. 201821815064.7 filed Nov. 6, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

This disclosure relates to an electronic cigarette.

Electronic cigarettes atomize nicotine-containing e-liquid.

Conventionally, the atomizing assembly fixedly communicates with the battery assembly. This increases the difficulty in replacing the atomization core.

SUMMARY

The disclosure provides an electronic cigarette.

Provided is an electronic cigarette, comprising an atomizing assembly and a battery assembly. The atomizing assembly is disposed on the battery assembly.

The atomizing assembly comprises a mouthpiece, a filter cotton, a guide tube, an e-liquid container, a first sealer adapted to seal the e-liquid container, a heating wire comprising a pin, a barrier, a base, a second sealer adapted to seal the base, an insulation ring, and electrodes. The battery assembly comprises a battery frame, a light guide, a silica gel, a fixed seat, a printed circuit board assembly, and a battery cell.

The guide tube is disposed in the e-liquid container. The heating wire is disposed on the barrier. The barrier is disposed in the base. The insulation ring passes through the pin of the heating wire and is fixed in the base. The electrodes are disposed in the insulation ring. The first sealer sleeves the guide tube and is disposed on the e-liquid container. The filter cotton is disposed on an upper surface of the first sealer. The mouthpiece covers the first sealer. The mouthpiece is connected to the e-liquid container. The second sealer is embedded in the base and is disposed at one side of the e-liquid container. The heating wire stretches out on the barrier; and the battery cell is welded to the printed circuit board assembly. The printed circuit board assembly is disposed on the fixed seat. The silica gel is disposed on one end of the fixed seat. The fixed seat is disposed in the battery frame, and the light guide is disposed on the battery frame.

Advantages of the electronic cigarette according to embodiments of the disclosure are summarized as follows. The e-liquid container comprises protrusions. The battery frame comprises pits corresponding to the protrusions. The atomizing assembly communicates with the battery assembly via the pits and the protrusions. The heating wire stretches out on the barrier. The stretched heating wire can sufficiently adsorb the e-liquid, prolonging the service life of the electronic cigarette.

DETAILED DESCRIPTION

To further illustrate, embodiments detailing an electronic cigarette are described below. It should be noted that the following embodiments are intended to describe and not to limit the disclosure.

Figure 1:
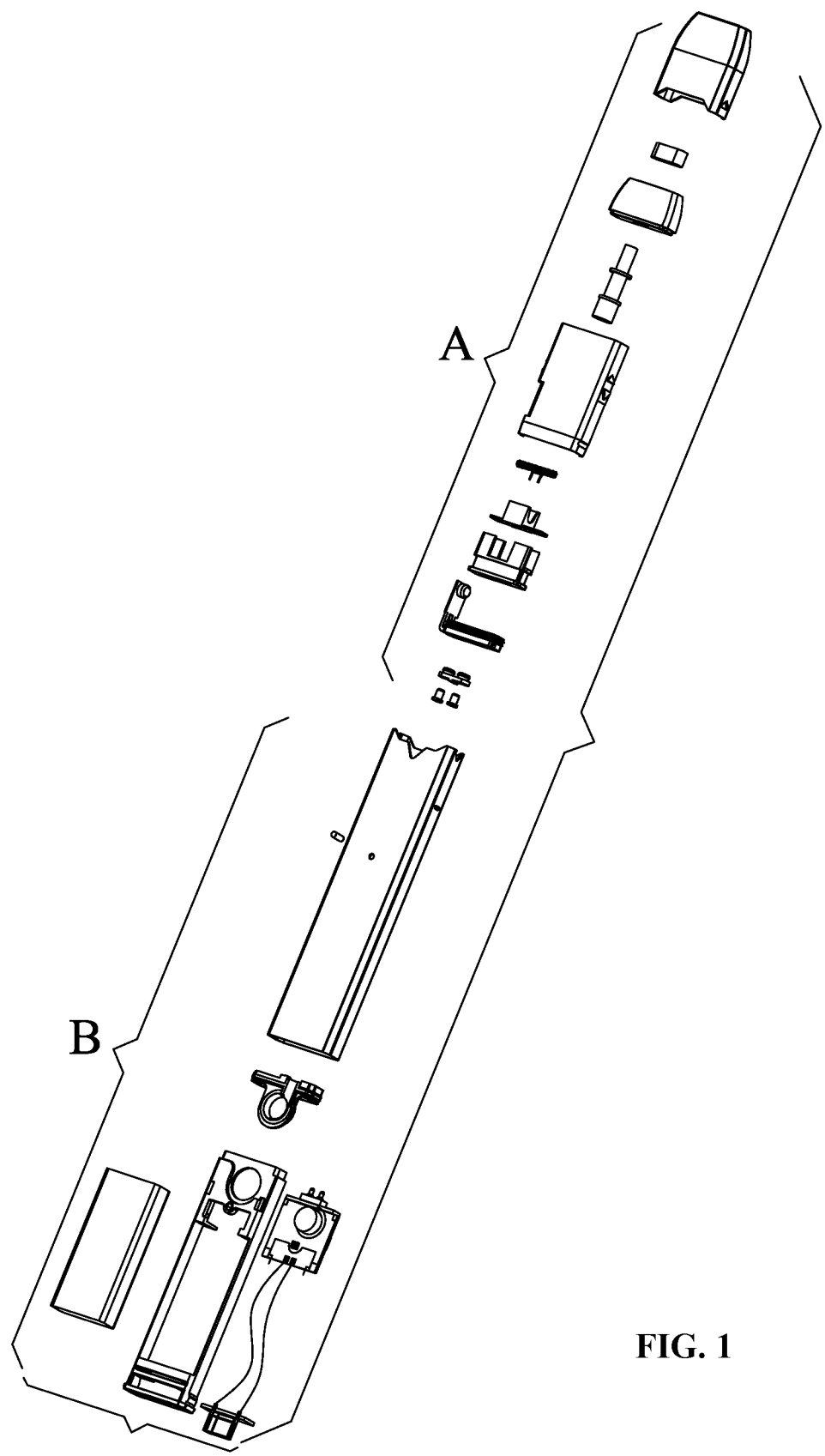
FIG. 1 is an exploded view of an electronic cigarette as described in the disclosure.
Figure 2:
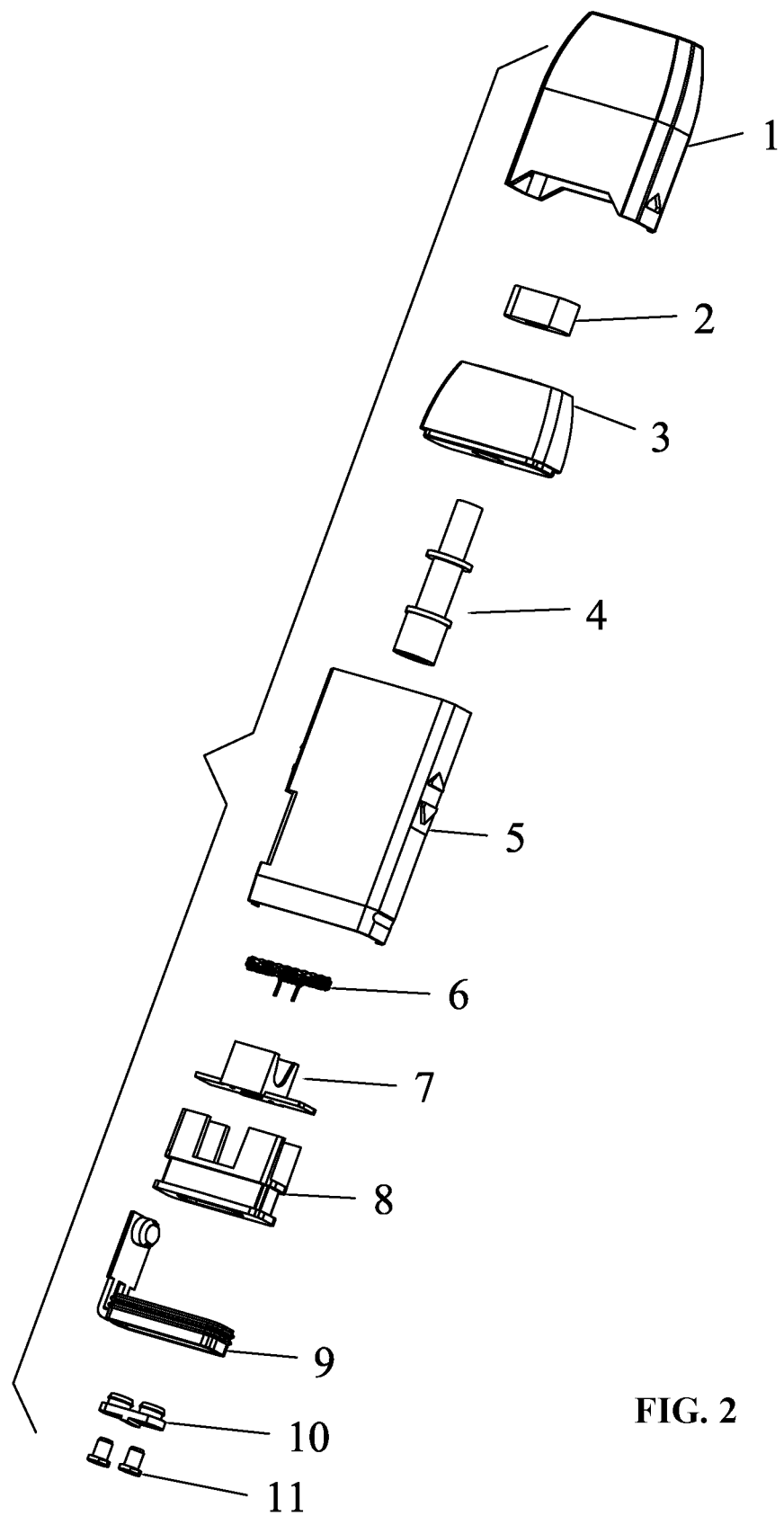
FIG. 2 is an exploded view of an atomizing assembly of an electronic cigarette as described in the disclosure.
Figure 3:
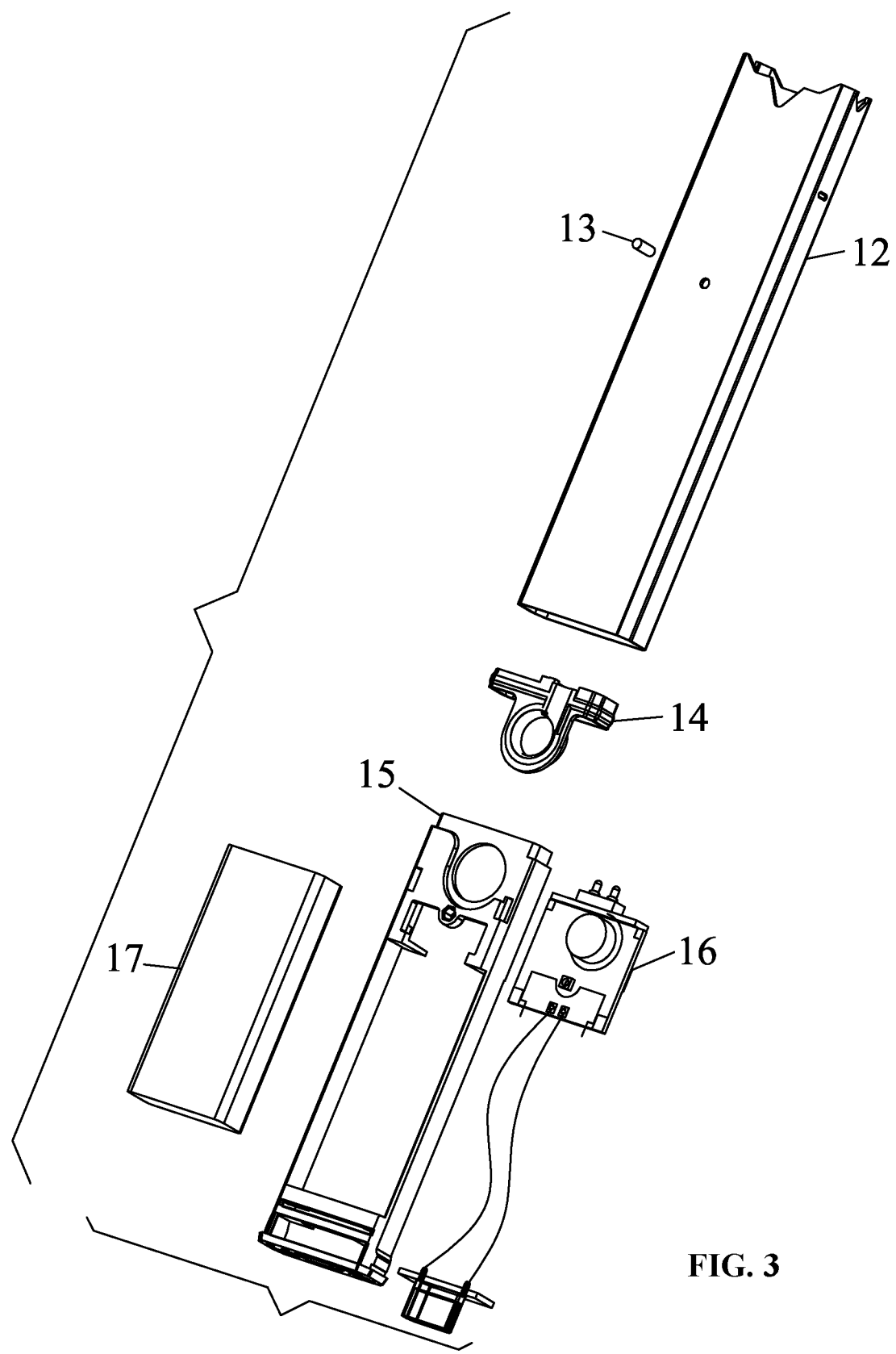
FIG. 3 is an exploded view of a battery assembly of an electronic cigarette as described in the disclosure.
Figure 4:
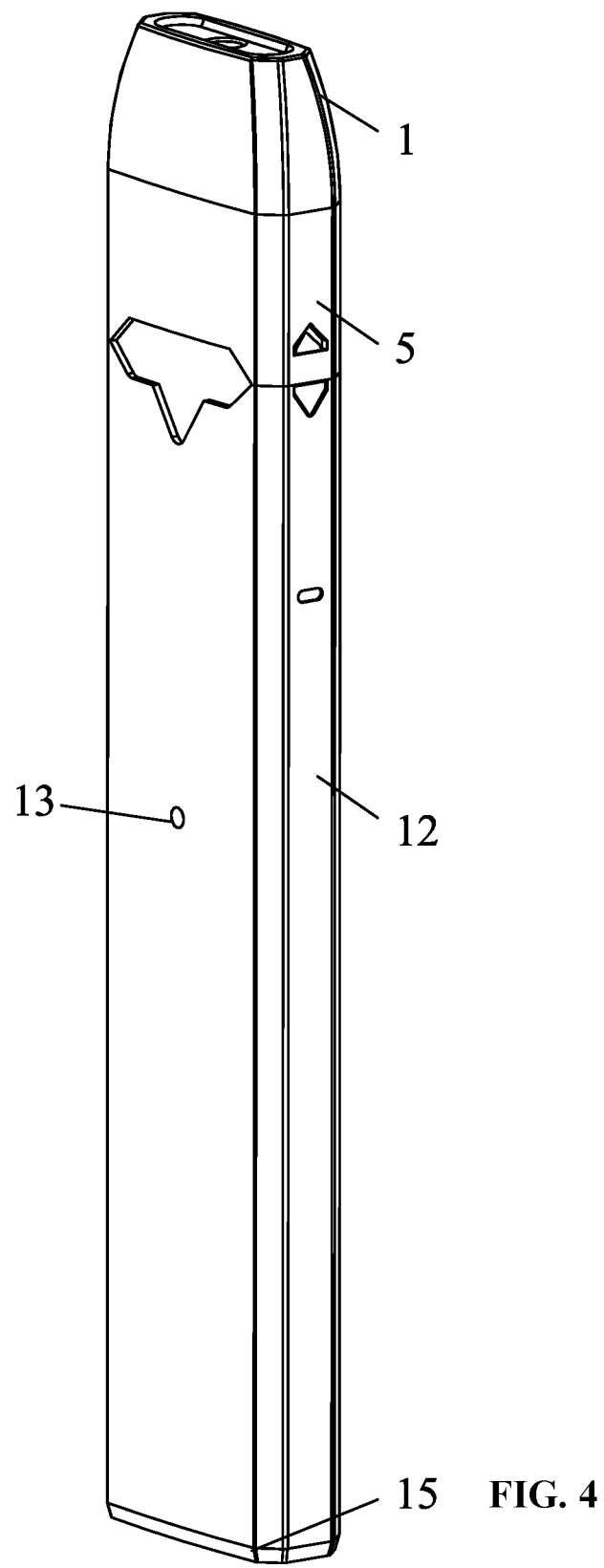
FIG. 4 is a stereogram of an electronic cigarette as described in the disclosure.
Figure 5:
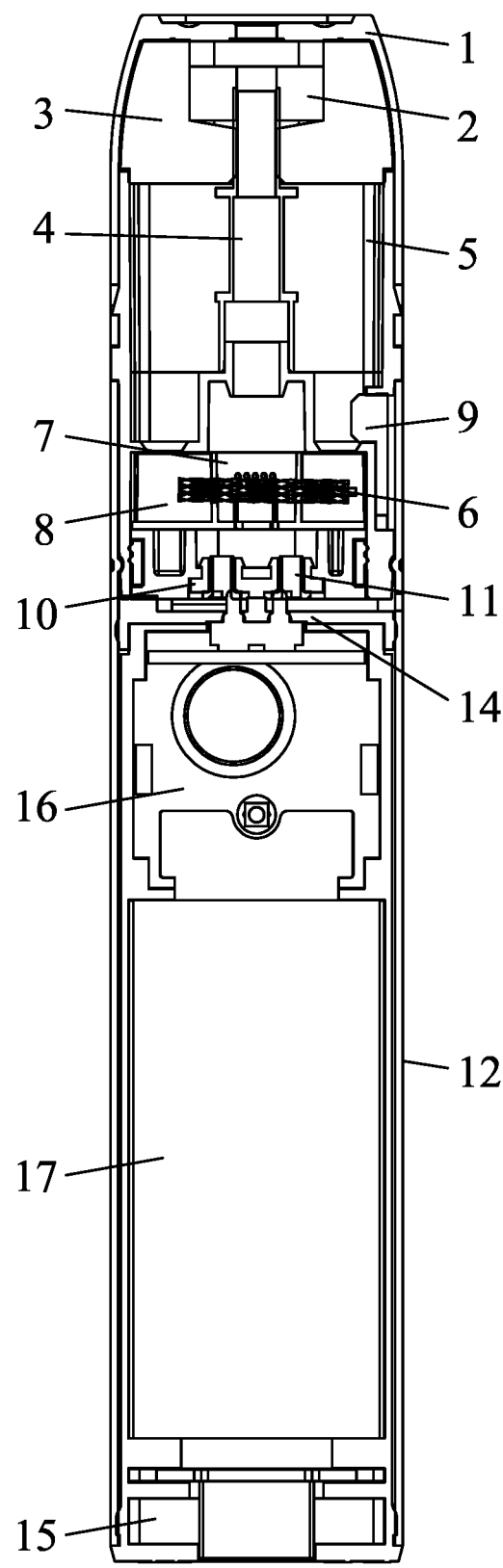
FIG. 5 is a sectional view of an electronic cigarette as described in the disclosure.

As shown in FIGS. 1-5, provided is an electronic cigarette, comprising: an atomizing assembly A; and a battery assembly B. The atomizing assembly A is disposed on the battery assembly B.

The atomizing assembly A comprises a mouthpiece 1, a filter cotton 2, a guide tube 4, an e-liquid container 5, a first sealer 3 adapted to seal the e-liquid container 5, a heating wire 6 comprising a pin, a barrier 7, a base 8, a second sealer 9 adapted to seal the base 8, an insulation ring 10, and electrodes 11. The battery assembly B comprises a battery frame 12, a light guide 13, a silica gel 14, a fixed seat 15, a printed circuit board assembly 16, and a battery cell 17.

The guide tube 4 is disposed in the e-liquid container 5. The heating wire 6 is disposed on the barrier 7. The barrier 7 is disposed in the base 8. The insulation ring 10 passes through the pin of the heating wire and is fixed in the base 8. The electrodes 11 are disposed in the insulation ring 10. The first sealer 3 sleeves the guide tube 4 and is disposed on the e-liquid container 5. The filter cotton 2 is disposed on the upper surface of the first sealer 3 to filer the e-liquid. The mouthpiece 1 covers the first sealer 3. The mouthpiece 1 is connected to the e-liquid container 5. The second sealer 9 is embedded in the base 8 and is disposed at one side of the e-liquid container 5. The second sealer 9 can be directly detached from the e-liquid container 5, which facilitates the loading of the e-liquid. The heating wire 6 stretches out on the barrier 7 and is carried by the base 8 to enter the e-liquid container 5. The heating wire 6 is free of being squeezed from other parts, so it is durable; in addition, the stretched heating wire can sufficiently adsorb the e-liquid, thus prolonging the service life of the electronic cigarette.

The battery cell 17 is welded to the printed circuit board assembly 16. The printed circuit board assembly 16 is disposed on the fixed seat 15. The silica gel 14 is disposed on one end of the fixed seat 15. The fixed seat 15 is disposed in the battery frame 12, and the light guide 13 is disposed on the battery frame 12.

The e-liquid container 5 comprises protrusions. The battery frame 12 comprises pits corresponding to the protrusions. The atomizing assembly communicates with the battery assembly via the pits and the protrusions. The electronic cigarette is flat, lightweight, and easy to carry.

It will be obvious to those skilled in the art that changes and modifications may be made, and therefore, the aim in the appended claims is to cover all such changes and modifications.

What is claimed is:

1. An electronic cigarette, comprising:

an atomizing assembly, the atomizing assembly comprising a mouthpiece, a filter cotton, a guide tube, an e-liquid container having a hole in a side wall, a first sealer adapted to seal the e-liquid container, a heating wire comprising a pin, a barrier, a base, a second sealer adapted to seal the base, an insulation ring, and electrodes; and a battery assembly, the battery assembly comprising a battery frame, a light guide, a silica gel, a fixed seat, a printed circuit board assembly, and a battery cell;

wherein:

the atomizing assembly is disposed on the battery assembly;

the guide tube is disposed in the e-liquid container;

the heating wire is disposed on the barrier; the barrier is disposed in the base; the insulation ring passes through the pin of the heating wire and is fixed in the base; the electrodes are disposed in the insulation ring;

the first sealer sleeves the guide tube and is disposed on the e-liquid container; the filter cotton is disposed on an upper surface of the first sealer; the mouthpiece covers the first sealer; the mouthpiece is connected to the e-liquid container;

the second sealer has an L-shape, one side of the second sealer is embedded in the base, the other side of the second sealer has a protruding part, and is disposed at one side of the e-liquid container with the protruding part sealing the hole of the e-liquid container; the heating wire stretches out on the barrier; and the battery cell is welded to the printed circuit board assembly; the printed circuit board assembly is disposed on the fixed seat; the silica gel is disposed on one end of the fixed seat; the fixed seat is disposed in the battery frame, and the light guide is disposed on the battery frame.

2. The electronic cigarette of claim 1, wherein the e-liquid container comprises a protrusion, and the battery frame comprises a pit matching with the protrusion.

* * * * *